United States Patent [19]

Funahashi et al.

[11] Patent Number: 4,643,979

[45] Date of Patent: Feb. 17, 1987

[54] METHOD FOR DETECTING PHOSPHORUS SEGREGATES IN STEEL

[75] Inventors: Yoshiko Funahashi; Yasuharu Matsumura; Senichi Harimaya; Yoshikazu Kamino; Hidenari Kitaoka, all of Chiba, Japan

[73] Assignee: Kawasaki Steel Corporation, Kobe, Japan

[21] Appl. No.: 670,924

[22] Filed: Nov. 13, 1984

[30] Foreign Application Priority Data

Nov. 14, 1983 [JP] Japan .............................. 58-213497

[51] Int. Cl.$^4$ ............................................. G01N 33/20
[52] U.S. Cl. ..................................... 436/78; 436/103; 436/169; 436/175
[58] Field of Search .................. 436/78, 103, 169, 175

[56] References Cited

U.S. PATENT DOCUMENTS 3,796,543  3/1974  Kamphake ........................ 23/230 R
4,420,567  12/1983  McMahon et al. ................ 436/103

FOREIGN PATENT DOCUMENTS 873319  4/1953  Fed. Rep. of Germany .
22895   2/1979  Japan ..................................... 436/78

OTHER PUBLICATIONS

Chemical Abstracts, vol. 26, 1932, p. 5871, Columbus, Ohio, U.S., M. Niessner; "New Methods for Identifying Minor Constituents of Alloys and for Detecting Segregation in Metal-Working Materials", and Mikrochemie 12, 1-24 (1932).

Chemical Abstracts, vol. 41, 1947, col. 6171 d-f, Columbus, Ohio, U.S.; H. L. Katz et al: "Direct Colorimetric Method for Phosphorus in all Types of Steel" and Anal. Chem. 19, 612-14 (1947).

Chemical Abstracts, vol. 40, 1946, col. 7065-7069, Columbus, Ohio, U.S.; N. D. Ivanova et al.: "Colorimetric Determination of Phosphorus in Iron Alloys" and Zavodskaya Lab. 12, 246-8 (1946).

T. S. Harrison, The Determination of Phosphorus in Heaematite Iron and Steel by The Molybdenum Blue Method, J.S.C.I., 68, Mar. 1949, pp. 84-88.

*Primary Examiner*—David L. Lacey
*Attorney, Agent, or Firm*—Young & Thompson

[57] ABSTRACT

Phosphorus segregates formed in cast steel upon solidifying are detected by a novel method comprising applying a metal etching reagent, for example, lithium chloride in ethanol, to a surface area of the steel to be examined, and attaching a sheet of test paper bearing an aqueous solution of silver nitrate to said surface, thereby detecting phosphorus segregates as stains on the sheet.

11 Claims, 4 Drawing Figures

METHOD FOR DETECTING PHOSPHORUS SEGREGATES IN STEEL

BACKGROUND OF THE INVENTION

This invention relates to a method for detecting phosphorus segregates, and more particularly, to such a method capable of rapidly and easily detecting the distribution of phosphorus in continuously cast steel slabs or large-sized steel ingots.

Heretofore, segregation in large-sized steel ingots has been judged by sulfur printing. This method is by attaching photographic paper impregnated with aqueous sulfuric acid to a polished cross section of a large-sized steel ingot, thereby detecting hydrogen sulfide given off from segregated sulfur as stains on the photographic paper. This method has been widely used on the production line. Recently, however, steels subjected to low sulfide treatment and Ca treatment, such as steels resistant to hydrogen embrittlement cracking, have been put into practical use, and much progress has been made in the art to manufacture high purity steel and to prevent segregation in continuous castings. In such advanced steels having extremely low sulfur contents it is difficult to detect solidification segregates by the conventional sulphur printing.

Aside from the sulfur printing, a macroanalyzer is known as a device for examining the segregation of alloying elements. The macroanalyzer can quantitatively evaluate a planar section of a large-sized steel ingot by applying an electron beam to the section and detecting the spectrum of X-rays generated as in EPMA. However, this method is not applicable to a commercial production process because it uses an expensive device, the surface to be examined must be finished by emery paper of the order of #1,000, the measurement of a sample takes more than one hour, the configuration of a sample is limited, it cannot be applied to a wide section sample, and so on.

Accordingly it is an object of this invention to provide a novel improved method capable of rapidly detecting segregates in Ca-loaded steels and low-sulfide steels over a large surface area as easily as by the sulfur printing method. In this method, the element to be detected in place of sulfur is phosphorus, which has the great likelihood to segregate upon solidifying, and phosphorus segregates are detected on test paper as stains.

One known method of detecting phosphorus is the phosphor printing reported by M. Niessner in 1932. This method is by attaching filter paper which has been immersed in liquid B shown below in Table 1 to a surface of steel to be examined for 3-5 minutes, removing the paper from the steel surface, and thereafter dipping the filter paper into liquid A for 3-4 minutes, thereby producing a printed image. Beause of unclear printed images and low sensitivity, it is difficult to detect with this method phosphorus segregates in commercial grade steels. Also it requires an additional procedure of dipping the filter paper in another liquid after removal from a steel surface.

TABLE 1

| Liquid A | |
|---|---|
| Stannous chloride saturated solution | 5 ml |
| Concentrated hydrochloric acid | 50 ml |
| Water | 100 ml |
| Alum | minor amount |

TABLE 1-continued

| Liquid B | |
|---|---|
| Ammonium molybdate | 5 g |
| Water | 100 ml |
| Nitric acid (specific gravity 1.2) | 35 ml |

It is therefore, another object of the present invention to provide a novel method for detecting phosphorus segregation which takes the place of the conventional phosphor printing method, can produce a clear printed image with high sensitivity through an easy printing operation, and is suitable for use in the control of an in-place production process.

SUMMARY OF THE INVENTION

Briefly, the present invention provides a method for detecting phosphorus segregates in solidified steel, comprising the steps of applying a metal etching reagent to a surface area of the steel to be examined, and attaching a test sheet bearing a solution of a heavy metal salt to said surface, thereby detecting phosphorus segregates as stains on the sheet.

DETAILED DESCRIPTION OF THE INVENTION

Figure 1A:
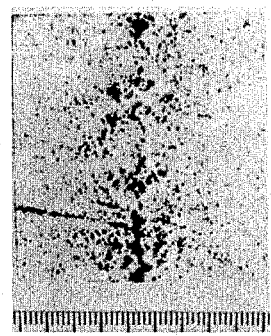
FIGS. 1a and 2a are photographic phosphorus prints showing phosphorus segregates in continuously cast billets according to the present invention.

Phosphorus (P) is likely to segregate upon solidification next to sulfur (S) and boron (B), and thus concentrates remarkably at the last-to-solidify site. An increased phosphorus content accelerates the rate of corrosion of steel. It is thus believed that segregated parts in solidified steel slabs or billets would be preferentially dissolved in etching liquid.

One of the inventors reported that when a steel specimen is anodized in an electrolyte based on an alcohol, phosphorus present in a solid solution form in the steel is converted to a phosphorus-containing oxo acid as the matrix is dissolved, which in turn, reacts with eluted iron ion to form an Fe—P—O—H compound (see Japanese Patent Application No. 58-119853). The present invention makes use of such an Fe—P—O—H compound to detect phosphorus segregates in cast steel. Fe—P—O—H compounds are difficultly soluble in alcohol and deposit simultaneously with their formation at the site of eluted phosphorus in steel. When the steel is gently washed by alcohol and air dried with a dryer, air exposure causes the Fe—P—O—H compound which has deposited at the site of phosphorus segregates to automatically give rise to a redox reaction so that it is decomposed to give off phosphine. The principle of the present invention is based on the detection of phosphine. It is believed that phosphine is given off when an oxo acid having a low oxidation number is decomposed as shown in the following formula.

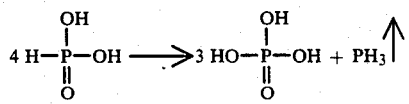

It is thus essential for the phosphorus in solid solution to be converted into an oxo acid having a low oxidation number as the matrix is dissolved. This conversion is promoted by an alcohol used as the solvent of the etching solution. The amount of the Fe—P—O—H compound formed largely depends upon the nature of the etching solution, and is increased as the concentration of acid in the solution is increased, and when the etching solution is free of a complexing agent capable of forming a complex with iron ion, or if present, as the complexing ability of the agent is reduced. The metal etching reagent used herein may be selected from ordinary reagents for use in observing metal structure which contain (a) at least one member selected from the group consisting of mineral acids such as hydrochloric acid, sulfuric acid, perchloric acid, phosphoric acid, nitric acid, etc.; organic acids such as picric acid, salicyclic acid, sulfosalicylic acid, acetic acid, formic acid, lactic acid, malic acid, etc.; and salts such as lithium chloride, copper chloride, iron chloride, tin chloride, zinc chloride, aluminum chloride, copper sulfate, copper nitrate, tetramethylammonium chloride, etc., in (b) an alcohol or water-containing alcohol solvent. The alcohol used herein may be any desired one as long as it is liquid at room temperature, with methanol, ethanol, and propanol being preferred.

After the surface of steel to be examined is etched in this way to generate phosphine from phosphorus segregates, a test sheet impregnated with a silver nitrate solution is attached to the surface. Phosphine acts to reduce silver cation into metallic silver which appears as stains on the test sheet, thereby detecting phosphorus segregates. This mechanism is observed at low concentrations of silver nitrate. At high concentrations, silver is directly reduced by the matrix iron.

The detecting solution is not limited to silver nitrate solution and use may be made of solutions of heavy metal salts such as gold chloride, copper chloride, silver bromide and silver iodide.

The test sheets used in the invention may be sheets of such materials as wood and synthetic resin as well as sheets of paper and, more preferably baryta paper having barium sulfate coated on the surface. The test sheet must bear an aqueous silver nitrate solution before it is pressed against the steel surface to be examined for phosphorus segregation. In most cases, the test sheet is impregnated with the solution. In some cases, the test sheet may be coated with the solution as by brushing immediately before it is attached to the steel surface. The concentration of heavy metal salt (color producing reagent) in the solution with which test sheets are impregnated or coated should be 0.1–80% by weight. At concentrations of less than 0.1%, stains or discolored spots on a print are too blurred to ensure the detection of segregated phosphorus. At concentrations of more than 80% the heavy metal salt precipitates on the sheet to render it unusable. By pressing the test sheet against a surface to be examined for several minutes, a clear print is obtained.

The test sheet after printing is immersed in an aqueous solution of 20% to 30% of sodium thiosulfate for about 5 minutes for fixing, and washed with running water. After drying, it is ready for storage.

Examples of the present invention will be presented by way of illustration and not by way of limitation.

Figure 2A:
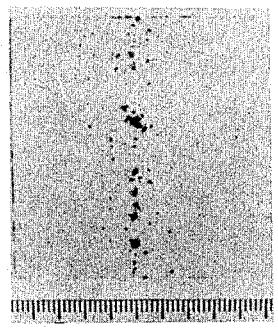

A cross section of a segregated part of a continuously cast billet of ordinary carbon steel containing 0.02% P was polished with #240 emery paper and cleaned with cotton wadding soaked with ethanol. The cleaned surface was etched and printed under the conditions shown in Table 2, and the color development examined. The results for two different types of billets are shown in FIGS. 1a and 2a.

TABLE 2
Phosphorus Printing Conditions

Figure 1B:
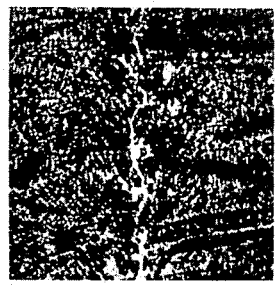
FIGS. 1b and 2b are macroanalyzer photographs showing phosphorus segregates in the same billets.
Figure 2B:
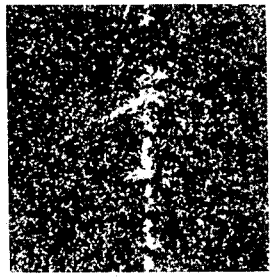

Etching conditions
  Etching liquid: 10 vol % acetylacetone,
                 3 wt % thenoyltrifluoroacetone, and
                 1 wt % lithium chloride in ethanol
  Temperature: room temperature
  Time: 2 minutes
Printing conditions
  Color producing solution: 5 wt % $AgNO_3$ in a 1:1 mixture of water and ethanol
  Contact time: 1 minute FIGS. 1b and 2b are the measurements of the phosphorus distribution on the two different billets by a macroanalyzer. The prints of phosphorus distribution shown in FIGS. 1a and 2a conform closely to the macroanalyzer measurements shown in FIGS. 1b and 2b, proving that this invention is sufficiently effective in detecting segregated phosphorus. It is to be noted that phosphorus prints as shown in FIGS. 1a and 2a are mirror images of macroanalyzer measurements as shown in FIGS. 1b and 2b respectively.

As seen from the examples, the method of the present invention can detect phosphorus segregates in a short time, i.e., two minutes of etching time and one minute of printing time; furthermore, unlike the sulfur printing, it eliminates troublesome operation in a dark room. In addition, it is very effective and useful in commercial lines because it can detect phosphorus segregates during in-place steel casting without the need for a mechanical device and without limitation on the size and configuration of steel products to be tested. It has been found that this invention allows phosphorus to be adequately detected even at concentrations as low as 30 parts per million parts of the matrix.

We claim:

1. A method for detecting phosphorus segregates in solidified steel, comprising the steps of
   applying a metal etching reagent to a surface area of the solidified steel to be examined, said metal etching reagent causing the eventual formation of phosphine, and
   applying a test sheet bearing a solution of a heavy metal salt against said surface area, thereby detecting phosphorus segregates as stains on the sheet.

2. The method according to claim 1 wherein the metal etching reagent is a solution of an acid or salt thereof in an alcohol.

3. The method according to claim 2 wherein the acid or salt is selected from the group consisting of mineral acids, organic acids, and salts thereof.

4. The method according to claim 3 wherein the etching reagent is lithium chloride.

5. The method according to claim 2 wherein the alcohol is selected from the group consisting of methanol, ethanol, and propanol.

6. The method according to claim 1 wherein the heavy metal salt is selected from silver nitrate, silver bromide, silver iodide, gold chloride, and copper chloride, and is dissolved in water.

7. The method according to claim 1 wherein the heavy metal salt solution contains 0.1 to 80% by weight of the heavy metal salt in water.

8. The method according to claim 1 wherein the heavy metal salt solution is an aqueous solution containing 0.1 to 80% by weight of silver nitrate.

9. The method according to claim 1 wherein the test sheet is paper.

10. The method according to claim 1 wherein the test sheet is pressed against the steel surface for a sufficient time to provide a printed image.

11. The method according to claim 10 which further comprises immersing the test sheet, after removal from the steel surface, in a solution of sodium thiosulfate for a sufficient time to fix the printed image.

* * * * *